(12) United States Patent
Li et al.

(10) Patent No.: US 11,844,753 B2
(45) Date of Patent: Dec. 19, 2023

(54) TRANSDERMAL DRUG DELIVERY SYSTEM FOR DELIVERING A DRUG TO A PATIENT

(71) Applicants: Weiyong Li, Doylestown, PA (US); Chi Luo, New Hope, PA (US)

(72) Inventors: Weiyong Li, Doylestown, PA (US); Chi Luo, New Hope, PA (US)

(*) Notice: Subject to any disclaimer, the term of this patent is extended or adjusted under 35 U.S.C. 154(b) by 0 days.

(21) Appl. No.: 17/983,392

(22) Filed: Nov. 8, 2022

(65) Prior Publication Data

US 2023/0147389 A1    May 11, 2023

Related U.S. Application Data

(60) Provisional application No. 63/277,098, filed on Nov. 8, 2021.

(51) Int. Cl.
  *A61K 9/70*   (2006.01)
  *A61K 31/192*  (2006.01)
  (Continued)

(52) U.S. Cl.
  CPC ........ *A61K 9/7084* (2013.01); *A61F 13/0246* (2013.01); *A61K 9/703* (2013.01);
  (Continued)

(58) Field of Classification Search
  CPC . A61K 9/7084; A61K 31/192; A61F 13/0246; A61F 2013/00646;
  (Continued)

(56) References Cited

U.S. PATENT DOCUMENTS

| 3,964,482 A | 6/1976 | Gerstel |
| 4,626,539 A | 12/1986 | Aungst |

(Continued)

FOREIGN PATENT DOCUMENTS

| EP | 0305026 A2 | 3/1989 |
| EP | 0439344 A2 | 7/1991 |
| EP | 2512446 B1 | 4/2015 |

OTHER PUBLICATIONS

Alpern, E.R., Henretig FM. Fever. Fleisher GR, Ludwg S, Henretig FM, eds. "Textbook of Pediatric Emergency Medicine," 5th ed. Philadelphia, PA: Lippincott Wiliams & Wilkins, 2006, pp. 295-306.

(Continued)

*Primary Examiner* — Andrew J Mensh

(57) ABSTRACT

A system that transdermally delivers a drug to a patient can be used to reduce suffering from acute/chronical musculo-skeletal pain. The system includes a backing layer, an adhesive layer, a topical applicator, a suitable quantity of drug, and a quantity of topical carrier. The topical applicator is connected across and against the backing layer by the adhesive layer. The suitable quantity of drug and the quantity of topical carrier are homogenously mixed together as a topical medication, which is retained and dispensed from the topical applicator. The topical applicator includes a flat applicator body, a plurality of blunted spikes, and a containment rim. The flat applicator body is the structural base of the topical applicator. The containment rim is used to perimetrically confine the topical medication. The blunted spikes are used to increase the surface area of the topical applicator in order to improve its retention of the topical medication.

14 Claims, 11 Drawing Sheets

(51) Int. Cl.
*A61F 13/02* (2006.01)
*A61M 37/00* (2006.01)
*A61F 13/00* (2006.01)

(52) U.S. Cl.
CPC .......... *A61K 31/192* (2013.01); *A61M 37/00* (2013.01); *A61F 2013/00646* (2013.01); *A61F 2013/00906* (2013.01); *A61M 2037/0007* (2013.01)

(58) Field of Classification Search
CPC ......... A61F 2013/00906; A61M 37/00; A61M 2037/0007
USPC ...................................................... 604/307
See application file for complete search history.

(56) References Cited

U.S. PATENT DOCUMENTS

| | | | |
|---|---|---|---|
| 4,767,751 A | 8/1988 | Davis | |
| 4,956,171 A | 9/1990 | Chang | |
| 5,093,133 A | 3/1992 | Wisniewski | |
| 5,152,997 A | 10/1992 | Ebert | |
| 5,736,154 A | 4/1998 | Fuisz | |
| 5,817,332 A | 10/1998 | Urtti | |
| 5,866,143 A | 2/1999 | Elkhoury | |
| 5,891,462 A | 4/1999 | Carrara | |
| 5,902,602 A | 5/1999 | Muller | |
| 5,948,433 A | 9/1999 | Burton | |
| 6,011,022 A | 1/2000 | El Khoury | |
| 6,335,030 B1 | 1/2002 | Hoeck | |
| 6,756,052 B1 | 6/2004 | Koch | |
| 7,537,590 B2 | 5/2009 | Santini | |
| 8,696,637 B2 | 4/2014 | Ross | |
| 8,834,447 B2* | 9/2014 | Chen | A61K 31/7088 424/443 |
| 9,161,915 B2 | 10/2015 | Fossel | |
| 10,493,049 B2 | 12/2019 | Li | |
| 2003/0065294 A1 | 4/2003 | Pickup | |
| 2005/0037983 A1* | 2/2005 | Dinan | A61K 38/21 514/420 |
| 2006/0078604 A1 | 4/2006 | Kanios | |
| 2010/0256174 A1 | 10/2010 | Yamaguchi | |
| 2011/0098258 A1 | 4/2011 | Masini-Eteve et al. | |
| 2011/0224515 A1 | 9/2011 | Mir | |
| 2012/0238970 A1* | 9/2012 | Royds | A61K 9/7092 604/304 |
| 2013/0046244 A1 | 2/2013 | Kinuta | |
| 2014/0243788 A1 | 8/2014 | Cantor | |
| 2015/0246004 A1 | 9/2015 | Hillhouse | |
| 2016/0331678 A1 | 11/2016 | Chen | |
| 2017/0095431 A1 | 4/2017 | Andrews | |
| 2017/0224642 A1* | 8/2017 | Li | A61K 9/703 |
| 2018/0064655 A1 | 3/2018 | Yu | |

OTHER PUBLICATIONS

Singh G., "Recent considerations in nonsteroidal anti-inflammatory drug gastropathy," Am. J Med., 1998, 105(1B). pp. 31S-38S.

Singh, G .et al., "NSAID induced gastrointestinal complications: The ARAMIS perspective—1997. Arthritis, rheumatism, and aging medical information system," J Rheumatol. Suppl., 1998; 51, pp. 8-16.

Deny, S. et al., "Topical NSAIDs for acute musculoskeletal pain in adults (Review)," Cochrane Database of Systematic Reviews 2015, Issue 6. Art. No. CD007402.

Deny, S. et al., "Topical NSAIDs for chronic musculoskeletal pain in adults (Review)," Cochrane Database of Systematic Reviews 2 016, Issue 4. Art. No. CD007400.

Pradal, J., "Comparison of skin permeation and putative anti-inflammatory activity of commercially available topical products containing ibuprofen and diclofenac," Journal of Pain Research, 2020, 13, pp. 2805-2814.

Pellett, M.A. et al., "Comparison of permeability data from traditional diffusion cells and ATR-FTIR spectroscopy. Part I. Synthetic membranes," International Journal of Pharmaceutics, 1997, 154, pp. 205-215.

Pellett, M.A. et al., "Comparison of permeability data from traditional diffusion cells and ATR-FTIR spectroscopy. Part II. Determination of diffusional path lengths in synthetic membranes and human stratum corneum ," International Journal of Pharmaceutics, 1997, 154, pp. 217-227.

Russeau, et al., "investigation of the permeation of model formulations and a commercial ibuprofen formulation in Carbosil and human skin using ATR-FTIR and multivariate spectral analysis," International Journal of Pharmaceutics, 2009, 374, pp. 17-25.

* cited by examiner

TRANSDERMAL DRUG DELIVERY SYSTEM FOR DELIVERING A DRUG TO A PATIENT

The current application claims a priority to the U.S. provisional patent application Ser. No. 63/277,098 filed on Nov. 8, 2022.

FIELD OF THE INVENTION

The present invention relates generally to medical and laboratory equipment. More specifically, the present invention is methods, systems, apparatuses, and devices for facilitating transdermal delivery a drug to a patient.

BACKGROUND OF THE INVENTION

The field of medical and laboratory equipment is technologically important to several industries, business organizations, and/or individuals.

Transdermal (TD) drug delivery involves two major categories of products, namely TD patches and topical products. TD patches have a well-defined contact area with the skin that will allow more accurate administration of the drug from the drug-containing medium on the patch to the user through his/her skin. In addition, the drug delivery medium of the patch is protected when in use. Important products of TD patches include Duragesic® (fentanyl), Lidoderm (lidocaine) and Burtrans® (buprenorphine) for management of pain, Ortho Evra (Ethinyl estradiol and norelgestromin) as a contraceptive, Daytrana® (methylphenidate) for ADHD, and Neupro® (rotigotine) for Parkinson's.

Topical products are applied to a certain area of the skin and most of them are intended to affect only the local area to which they are applied. Examples include a local anesthetic (lidocaine and prilocaine), Pennsaid (diclofenac) for pain caused by osteoarthritis, and Lotrisone (betamethasone and clotrimazole) for reducing itching, swelling, and redness of the skin. An exception is Elestrin (estradiol), which is an example of transdermal drug delivery using a topical formulation for vasomotor symptoms (hot flash) due to menopause. But in general, topical products lack the mechanisms in controlling the rate of drug delivery through a fixed area of the user's skin.

Further, Nonsteroidal anti-inflammatory drugs (NSAIDs) are the most widely prescribed drugs in the world. There are over two dozen NSAIDs commercially available, most in various oral dosage forms, and some as topical formulations. Ibuprofen is an NSAID that is used widely for reducing fever in pediatric patients. It is estimated that 20% of the pediatric emergency visit is related to fever (Alpern E R, Henretig F M. Fever. Fleisher G R, Ludwg S, Henretig F M, eds. Textbook of Pediatric Emergency Medicine. 5th ed. Philadelphia, Pa.: Lippincott Williams & Wilkins; 2006. 295-306). Therefore, a TD ibuprofen formulation that can accurately deliver the active ingredient through the skin, particularly targeted for infants and toddlers, can have significant health benefits. Diclofenac has been approved in the U.S. as an analgesic medical product for topical applications.

Taking NSAIDs orally for long-term pain management has its risks. A 1998 report of oral NSAID-associated gastropathy documented that among 30 million Americans taking the drugs regularly every year, about 107,000 patients were hospitalized for NSAID-associated gastrointestinal (GI) complications (Singh G. Am J Med. 1998; 105 (1B): 31S-8S). Of those, an estimated 16,500 died due to NSAID-related complications among the arthritis patients alone (Singh G, Rosen Ramey D. J Rheumatol Suppl 1998; 51:8-16).

On the other hand, clinical results have demonstrated that topical NSAID products can be efficacious as a pain reliever and at the same time avoid the GI tract side effects. A 2015 Cochrane review of 61 clinical studies involving nearly 8,400 patients has shown that topical NSAID formulations containing diclofenac, ibuprofen, ketoprofen, piroxicam, and indomethacin can provide pain relief for patients with musculoskeletal injuries (acute conditions) such as sprains, strains, and overuse injuries (Derry_S, Moore_R A, Gaskell_H, McIntyre_M, Wi_en_P J. Cochrane Database of Systematic Reviews 2015, Issue 6. Art. No.: CD007402). No series of systemic adverse events were reported in those studies. Another Cochrane 2016 review of 39 clinical studies involving nearly 10,600 patients with chronic conditions have concluded that topical products containing diclofenac and ketoprofen "can provide good levels of pain relief beyond carrier in osteoarthritis for a minority of people, but there is no evidence for other chronic painful conditions". Data regarding serious GI-related adverse events were not available (Derry S, Conaghan P, Da Silva J A P, Wiffen P J, Moore R A. Cochrane Database of Systematic Reviews 2016, Issue 4. Art. No.: CD007400).

The lack lust performance of the NSAID topical products in relieving pain for chronic patients is not surprising considering the fact that a certain amount of the active ingredients have to penetrate and permeate through the skin to reach the site of inflammation and pain in order for them to be effective.

Current products of TD patches on the market are limited by their ability to deliver the drugs at certain rates. For example, the amounts of drug delivered in 24 hours for buprenorphine as an active ingredient, ritigotine as an active ingredient and rivastigmine as the active ingredient are delivered at rates of 0.12, 1, and 4.5 mg, respectively. The rate cannot easily increase because of the nature of the active ingredients and other factors. For example, first of all, a single TD patch can only carry a limited amount of the drug delivery medium, as well as the drug. Further, there are limited choices for the drug-delivering media, which usually consist of adhesive systems (for Matrix type). For some TD patch types, an added barrier (e.g., a membrane for the Reservoir system) is needed, which further limits the rate of drug delivery. These characteristics imply that a patch is not a drug delivery system for a drug that requires a higher dose to reach an effective level in a human body (i.e., in the range of 10-100 mg/24 hours). The topical products have performed worse as transdermal drug delivery systems. In a recent study, 12 topical products, six of each containing diclofenac or ibuprofen, were tested for in vitro permeation against human skin. The commercial formulations included emulsions, creams, and gels with either 1% diclofenac or 5-10% ibuprofen. Skin permeation varied widely among the formulations. The cumulative amount of drug that penetrated the skin over 24 hours ranged from 119 to 747 $ng/cm^2$ for products containing 1% diclofenac, and from 5944 to 9293 $ng/cm^2$ for products containing 5% ibuprofen (Pradal J. Journal of Pain Research. 2020:13, 2805-2814). The results show that drug penetration is very limited for these products.

There are various factors that control the rate of drug delivery for TD products which include 1) physical/chemical property of the active ingredient—TD drug delivery is a process of partitioning and diffusion of the drug molecules. The presence of the skin barrier, i.e., the stratum corneum (SC) layer, sets limits for the type of drugs that are suitable for TD delivery. For example, the molecular weight of the drug should be <500 Dalton; 2) formulation—most topical products are semi-solids in forms of, for example, gels, creams, ointments, and emulsions, which show significant differences in their ability to deliver drug trans dermally. Permeation enhancers are often adopted to facilitate drug delivery in these products; 3) solubility of the drug—the rate of drug penetration in TD drug delivery is positively correlated to the concentration of the active ingredient (dissolved) in a carrier of the topical formulation; 4) skin conditions of the patient—the SC layer of the skin provides the best protection to the human body when it is in the dry state. It is also the state that will prevent the drug from penetrating the skin. The application of a patch or a topical product will to a certain degree alter the skin condition to facilitate drug penetration through partial hydration of the skin's SC layer; 5) environment of drug application— TD patches create an occlusive environment when in use, which will cause the hydration of the SC layer. Some of the topical products, for example, ointments, can also create an occlusive environment to a lesser degree.

Further, various forms of TD patches are well accepted medical products and they serve important purposes in the health care community. But their commercial manufacturing requires sophisticated equipment and can be costly compared with topical products. Furthermore, the types of drugs and the amounts that can be delivered by TD patches are still very limited.

Therefore, there is a need for improved methods and systems for facilitating delivering a drug to a patient that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a transdermal drug delivery system for delivering a drug to a patient is disclosed. Further, the transdermal drug delivery system may include an applicator mounted on a backing layer of a medical tape via an adhesive layer and a topical formulation comprising a suitable amount of a drug. Further, the suitable amount of drug penetrates the skin upon applying the transdermal drug delivery system to the skin of a patient. Further, the topical formulation may include an EthoGel formulation comprising a suitable concentration of an active ingredient in a hydrogel-like carrier for delivering a given dose of the drug trans-dermally and two gelling agents which define the carrier's hydrogel-like physical properties in the presence of two skin penetration enhancers which also act as solvent/co-solvent. Further, the topical formulation may include buffering agents to increase the solubility of the active ingredient in the formulation, stabilizers, and various components with an optimized ratio to maintain the chemical and physical stability of the drug delivery medium. Further, the applicator may include a rim comprising a boundary defining a sealed space and blunt spikes present on a bottom surface of the applicator. Further, a height of the rim may be larger than a height of the blunt spikes. Further, the topical formulation may be filled in the sealed space of the applicator between the spikes and the rim.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

Figure 1:
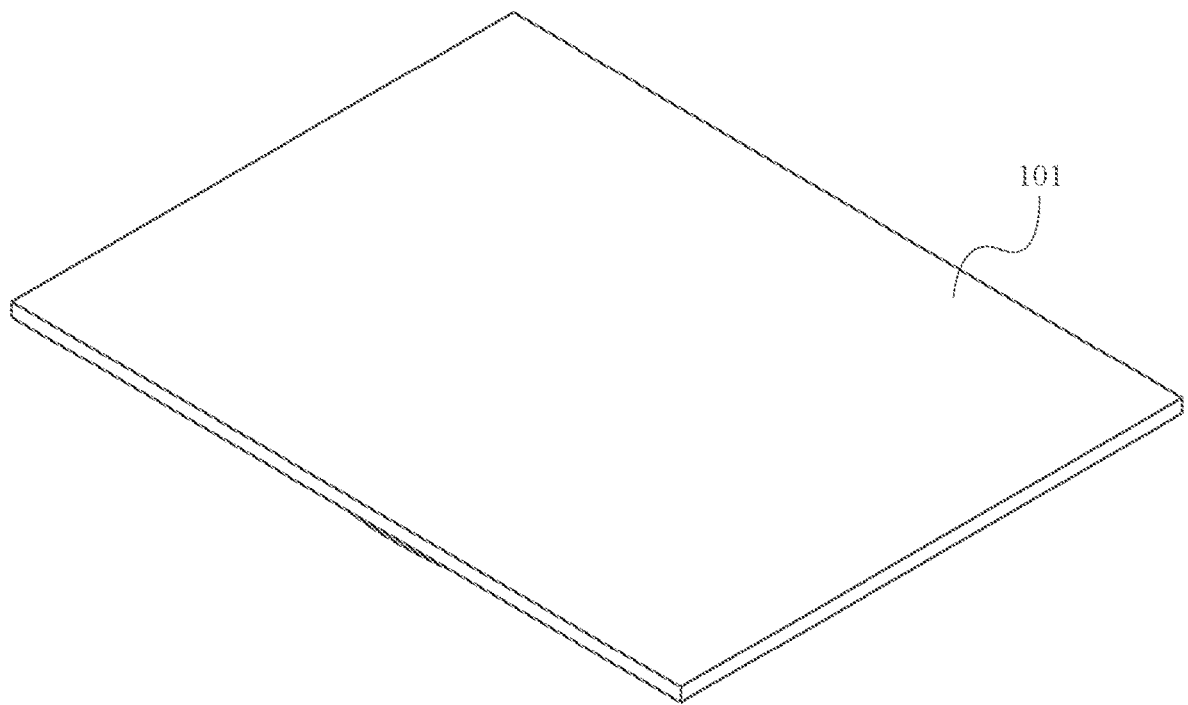
FIG. 1 is a top perspective view of the present invention.
Figure 2:
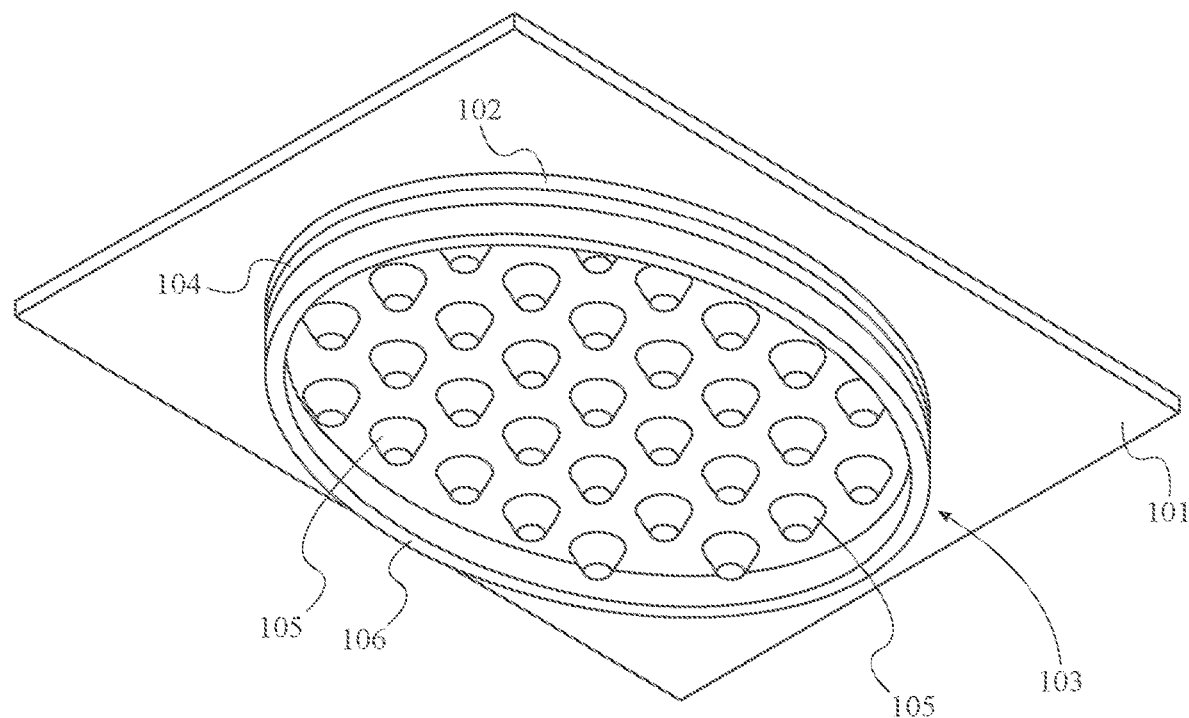
FIG. 2 is a bottom perspective view of the present invention.
Figure 3:
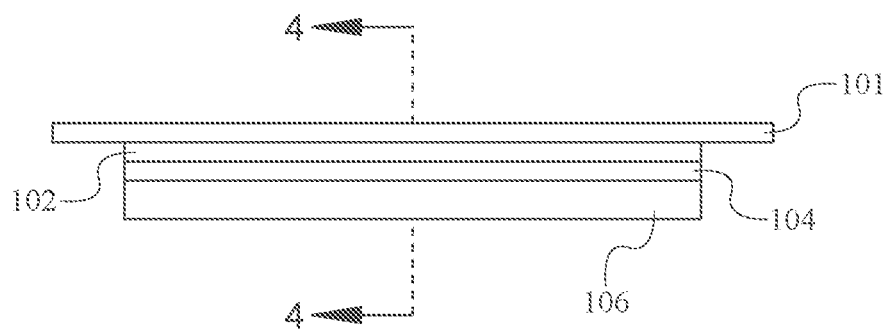
FIG. 3 is a side view of the present invention.
Figure 4:
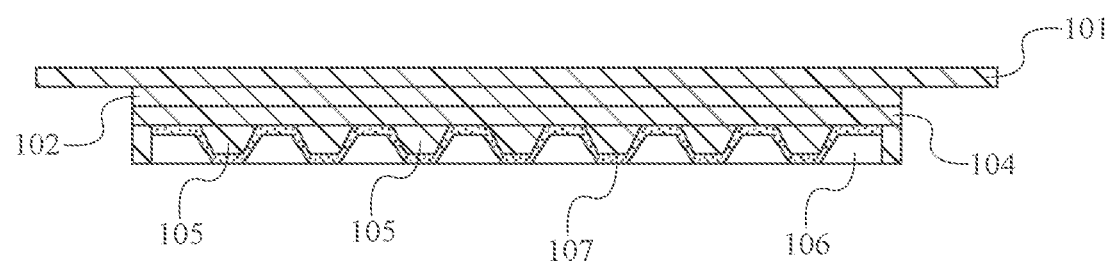
FIG. 4 is a cross-sectional view of taken along line 4-4 in FIG. 3.
Figure 5:
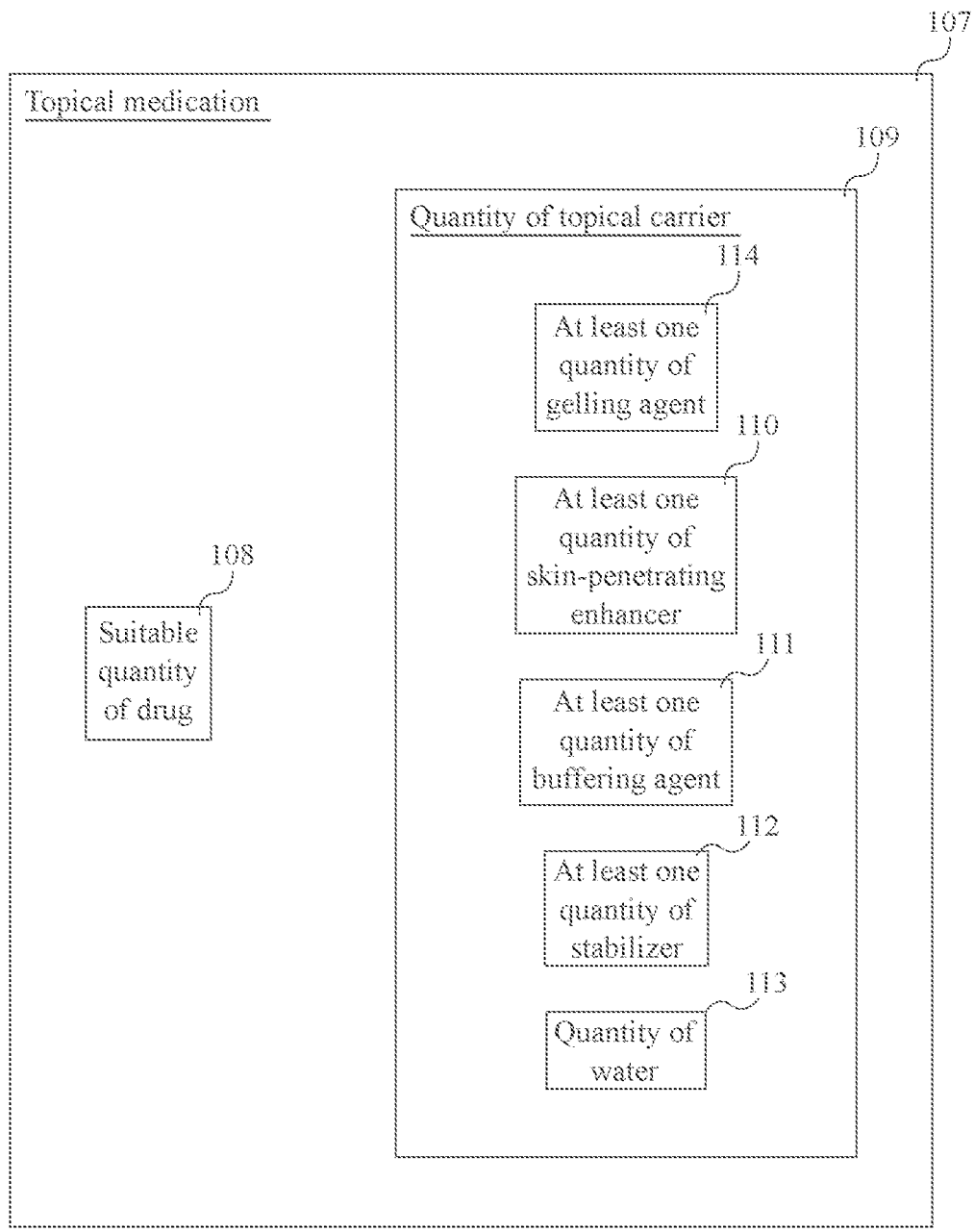
FIG. 5 is a block diagram illustrating composition of the topical medication for the present invention.

All illustrations of the drawings are for the purpose of describing selected versions of the present invention and are not intended to limit the scope of the present invention.

The present invention is a system for transdermally delivering a drug to a patient. The present invention can be used on a patient that has arthritis or is suffering from acute/chronical musculoskeletal pain. As can be seen in FIGS. 1 through 5, s preferred embodiment of the present invention comprises a backing layer 101, an adhesive layer 102, a topical applicator 103, a suitable quantity of drug 108, a quantity of topical carrier 109. The backing layer 101 is used as a structural base to connect the other components of the present invention together. The backing layer 101 is preferably a piece of medical tape and is preferably impermeable in order to prevent any medicinal fluid from seeping through the backing layer 101. The adhesive layer 102 allows the topical applicator 103 to be adhered onto the backing layer 101. The topical applicator 103 is used to retain and dispense the suitable quantity of drug 108 with the quantity of topical carrier 109. The topical applicator 103 is preferably made of a polycarbonate material. The suitable quantity of drug 108 is any medication that can be topically applied through a patient's skin. The suitable quantity of drug 108 can be, but is not limited to, a non-steroidal anti-inflammatory drug (NSAID). The quantity of topical carrier 109 allows for easy topical application and retention of the suitable quantity of drug 108. The quantity of topical carrier 109 can be, but is not limited to, a gel, a cream, a foam, a lotion, or an ointment.

The topical applicator 103 is also configured to assist in the easy topical application and retention of the suitable quantity of drug 108. The topical applicator 103 comprises a flat applicator body 104, a plurality of blunted spikes 105, and a containment rim 106. The flat applicator body 104 is used as a structural base to connect the other components of the topical applicator 103 together. The flat applicator body 104 may be sized and/or shaped to optimally deliver the suitable quantity of drug 108 through a patient's skin. For example, a perimeter shape of the flat applicator body 104 can be, but is not limited to, a square shape, a rectangular shape, a circular shape, or an oblong shape. The containment rim 106 is used as a perimeter boundary for the suitable quantity of drug 108 and the quantity of topical carrier 109. A height of the containment rim 106 from the flat applicator body 104 is preferably between 600 micrometers (μm) to 3500 μm. The plurality of blunted spikes 105 is used to increase the surface area of the topical applicator 103 that is available to retain the suitable quantity of drug 108 and the quantity of topical carrier 109. A total number of blunted spikes for the plurality of blunted spikes 105 may be configured to optimally deliver the suitable quantity of drug 108 through a patient's skin.

The general configuration of the aforementioned components allows the present invention to effectively and efficiently delivery a drug to a patient through the patient's skin. The suitable quantity of drug 108 and the quantity of topical carrier 109 are homogenously mixed together as a topical medication 107 so that the quantity of topical carrier 109 is able to dilute, retain, and dispense the suitable quantity of drug 108. The adhesive layer 102 is positioned in between the backing layer 101 and the flat applicator body 104, and, thus, the adhesive layer 102 allows the flat applicator body 104 to connect across and against the backing layer 101. This arrangement between the backing layer 101, the adhesive layer 102, and the flat applicator body 104 provides the topical applicator 103 with the necessary structural support as the topical medication 107 is administered to the patient with the present invention. The containment rim 106 and the plurality of blunted spikes 105 are positioned adjacent to the flat applicator body 104, opposite to the backing layer 101, which allows the containment rim 106 and the plurality of blunted spikes 105 to securely retain and readily dispense the topical medication 107 proximal to the patient's skin. The plurality of blunted spikes 105 is connected onto the flat applicator body 104, is distributed across the flat applicator body 104, and is oriented away from the flat applicator body 104. This arrangement for the plurality of blunted spikes 105 allows the topical applicator 103 to uniformly increase its available surface area and consequently allows the topical applicator 103 to retain a larger quantity of the topical medication 107 amongst the plurality of blunted spikes 105. The containment rim 106 is peripherally connected to the flat applicator body 104 and is positioned around the plurality of blunted spikes 105. This arrangement for the containment rim 106 allows the topical applicator 103 to perimetrically confine the topical medication 107 amongst the plurality of blunted spikes 105 and consequently allows the topical applicator 103 to retain the topical medication 107 within the containment rim 106.

The quantity of topical carrier 109 is preferably composed as a hydrogel-like carrier. Thus, the quantity of topical carrier 109 may comprise at least one quantity of gelling agent 114, at least one quantity of skin-penetrating enhancer 110, at least one quantity of buffering agent 111, at least one quantity of stabilizer 112, and a quantity of water 113. Moreover, the at least one quantity of gelling agent 114, the at least one quantity of skin-penetrating enhancer 110, the at least one quantity of buffering agent 111, the at least one quantity of stabilizer 112, and the quantity of water 113 are homogenously mixed together in order to compose the hydrogel-like carrier.

A first embodiment of the topical medication 107 is a hydrogel-like carrier with ibuprofen, and, thus, the suitable quantity of drug 108 is a quantity of ibuprofen. The at least one gelling agent 114 includes a quantity of xanthan gum and a quantity of carbomer. The at least one quantity of skin-penetrating enhancer 110 includes a quantity of ethanol and a quantity of glycerin. The at least one quantity of buffer agent includes a quantity of sodium carbonate. The at least one quantity of stabilizer 112 is a quantity of polyethylene glycol. Moreover, the compositional proportions of the first embodiment of the topical medication 107 are preferably the following. The quantity of ibuprofen is approximately 4.0 percentage by weight (wt. %) of the topical medication 107. The quantity of water 113 is approximately 41.0 wt. % of the topical medication 107. The quantity of xanthan gum is approximately 1.0 wt. % of the topical medication 107. The quantity of carbomer is approximately 0.2 wt. % of the topical medication 107. The quantity of ethanol is approximately 40.0 wt. % of the topical medication 107. The quantity of glycerin is approximately 10.5 wt. % of the topical medication 107. The quantity of sodium carbonate is approximately 0.35 wt. % of the topical medication 107. The quantity of polyethylene glycol is approximately 3 wt. % of the topical medication 107. In reference to the aforementioned compositional proportions of the first embodiment of the topical medication 107, the term "approximately" preferably means within an error range of up to ±0.5 wt. %.

A second embodiment of the topical medication 107 is a hydrogel-like carrier with diclofenac, and, thus, the suitable quantity of drug 108 is a quantity of diclofenac. The at least one gelling agent 114 includes a quantity of xanthan gum and a quantity of carbomer. The at least one quantity of skin-penetrating enhancer 110 includes a quantity of ethanol and a quantity of glycerin. The at least one quantity of buffer agent includes a quantity of sodium carbonate. Moreover, the compositional proportions of the second embodiment of the topical medication 107 are preferably the following. The quantity of diclofenac is approximately 1.0 wt. % of the topical medication 107. The quantity of water 113 is approximately 37.92 wt. % of the topical medication 107. The quantity of xanthan gum is approximately 0.80 wt. % of the topical medication 107. The quantity of carbomer is approximately 0.78 wt. % of the topical medication 107. The quantity of ethanol is approximately 38.8 wt. % of the topical medication 107. The quantity of glycerin is approximately 20.0 wt. % of the topical medication 107. The quantity of sodium carbonate is approximately 0.70 wt. % of the topical medication 107. In reference to the aforementioned compositional proportions of the second embodiment of the topical medication 107, the term "approximately" preferably means within an error range of up to ±0.5 wt. %.

Supplemental Description

The present disclosure describes methods, systems, apparatuses, and devices for facilitating delivering a drug to a patient trans-dermally. Further, the disclosed system may include an EthoGel-Applicator transdermal drug delivery system (EGATDDS) developed for delivery of nonsteroidal anti-inflammatory drugs (NSAIDs) and other drugs to patients. Further, the NSAID-containing formulation may include a hydrogel-like carrier and is intended to be used as a pain reliever for arthritis patients and anti-fever medicine for pediatric patients, the former application prefers localized drug delivery whereas the latter requires the active ingredient to reach the systemic circulation. The EGATDDS may be associated with an EthoGel formulation comprising up to 50% (w/w) ethanol or a combined ethanol+glycerin content up to 70% (w/w) which are utilized as the main solvent/co-solvent in the carrier and also as the skin permeation enhancers. By adjusting the total content and ratio of the two enhancers, it may be feasible either to make the skin a drug reservoir to retain the drug locally or to maximize the drug penetration across the skin to facilitate systemic drug delivery. To make the transdermal drug delivery system effective, the EthoGel formulation may be applied in combination with a disk-like applicator which is mounted on a backing layer of a medical tape via an adhesive layer, and which is applied over the skin of a patient to create an occlusive micro-environment for ensuring the desired rate of drug delivery while minimizing evaporation of the volatile component(s) in the EthoGel formulation.

Further, the disclosed transdermal drug delivery system may include the EthoGel formulation which is a topical formulation of a drug with a hydrogel-like carrier utilizing ethanol and glycerin as the main solvent/co-solvent, and an applicator that is mounted on a backing layer of a medical tape via an adhesive layer. Further, the applicator may include a rim to define a sealed space, in which blunt spikes are present on the surface of the applicator, and wherein the EthoGel formulation is filled in the space on the applicator between the spikes and the rim.

Further, the disclosed method may include delivering a drug in the EthoGel formulation to a patient by applying the transdermal drug delivery system to the skin of the patient.

Further, the EthoGel-Applicator transdermal drug delivery system (EGATDDS) may be designed to achieve improved and more controllable TD drug delivery compared with the TD patches and topical products. In vitro permeation studies were conducted to demonstrate the system's ability to deliver ibuprofen and diclofenac across abdominal pigskin. Further, the EthoGel Formulation may include ibuprofen or diclofenac as the active ingredient in a hydrogel-like carrier. Further, the rate of permeation may be determined using the Attenuated Total Reflection Fourier Transform Infrared Spectroscopy (ATR-FTIR), and multivariate modeling. The disclosed method allows the simultaneous quantitation not only for the active ingredients but also for the skin permeation enhancers. Further, the EGATDDS may achieve a flux of 5-324 $\mu g/cm2/H$ and 25-1337 $\mu g/cm^2/H$ for diclofenac and ibuprofen, respectively. The flux results may be obtained based on comprehensive in vitro permeation studies by using the pig abdominal skin samples, that may be normalized to reflect the equivalence of 0.10 cm skin thickness. For example, 36 different formulations have been tested for ibuprofen alone to optimize the formulation so that it is feasible to deliver a milligram scale of the active ingredient per hour transdermally when using an applicator with $\geq 10$ cm$^2$ in size.

Compared with the topical NSAID products currently on the market, the EGATDDS has its advantages. For instance, the EthoGel formulations (or formulations) contain a high concentration of multiple skin penetration enhancers, which speed up the TD drug delivery. Further, the formulations offer high solubility for the active ingredient. Further, the formulations may form a gel that is physically stable even in the presence of a very high concentration of organic solvents (i.e., ethanol and glycerin). Further, the EGATDDS offers an occlusive environment so that the skin's degree of hydration can be controlled to reduce the SC layer's barrier ability and therefore to facilitate faster drug penetration and permeation.

Further, the effectiveness of the EthoGel formulation to optimize transdermal delivery of the active ingredient from the dosage form suitable for the drug administration may be evaluated, before any pre-clinical or clinical study on patients or volunteers, by conducting in vitro skin permeation study, and the test may be used as a screening tool for formulation development. An ATR-FTIR-based setup, which was described by Pellett et al. in 1997 and Russeau et al. in 2009, may be used instead of the traditional Franz cell for the skin permeation test. Significant improvements may be to the setup to create the unique occlusive environment of the drug delivery system. A proprietary chemometric modeling method may be used to perform quantitative analysis based on spectral data. In addition, the method may be used to determine the concentration of the active ingredient dissolved in the EthoGel formulation.

In Vitro Permeation

The skin permeation study may be conducted using a Bruker ATR-FTIR instrument (Model Alpha; Bruker Optics Ltd., MA, USA) equipped with a 2×2 mm diamond spectral window. Pig abdominal skin samples may be obtained from a local meat supplier. The skin samples may be treated by removing the fat and connecting tissues from the dermis side, followed by cutting them into 2×2 cm-size pieces and keeping them at freezing temperature for later use. Further, skin thickness may be measured before the experiment by allowing the skin sample to warm to room temperature and by using a Material Thickness Meter (Model No. PCE-CT 26; PCE Americas Inc, Jupiter, Fla., USA).

In a typical experiment, the skin sample may be put on the spectral window of the spectrometer with the dermis side facing the window. Further, about 1 g of the EthoGel formulation may be applied on the stratum corneum side of the skin sample, which may be covered by an applicator with an area of 3.5 cm$^2$ to minimize the loss of permeation enhancers (i.e., ethanol) through evaporation from the formulation. IR spectra may be taken at 15-60 min intervals and the experiment may be continued for up to 72 hours when needed. Further, the spectra may be used for calculating w/w % of the active ingredient (ibuprofen or diclofenac), ethanol, and glycerin on the dermis side of the skin. Chemometric modeling may be conducted using the software Unscrambler (CAMO Software AS, Oslo, Norway). The diffusion coefficients of the active ingredient, ethanol, and glycerin can be calculated using the following equation:

$$D = \frac{h^2}{6L}$$

where D is the diffusion coefficient (cm2/H), L is the lag time (hour) and h is the skin thickness (cm). The lag time may be obtained from the plots in FIGS. 8-11, which may be obtained using the EthoGel formulation described in Example 1 (ibuprofen) and Example 2 (diclofenac).

The flux J (μg/cm2/H) is calculated using the following equation:

$$J = \frac{DC}{h}$$

where D is the diffusion coefficient, C is the concentration (μg/mL) of the active ingredient dissolved in the EthoGel formulation and h is the thickness of the skin.

Example 1 of EthoGel Formulation

When preparing this EthoGel formulation of ibuprofen on a 1 kg scale, 400 g of ethanol, 105 g of glycerin, 200 g of water, and 30 g of polyethylene glycol may be mixed in a suitable container under stirring. Further, 3.5 g of sodium carbonate, 40.0 g of ibuprofen, 10.0 g of xanthan gum, and 2.0 g of Carbomer may be added to dissolve/disperse while the mixture is under stirring. Further, a homogenizer may be used to help disperse xanthan gum and/or Carbomer if needed. After completing the addition of all the solid ingredients, keep stirring for 30 min, followed by slowly adding the remaining amount of water (209.5 g) under slow stirring until the mixture becomes a homogeneous gel. An in vitro permeation study for this formulation using the pig abdominal skin (thickness=0.19 cm) shows that ibuprofen has a flux of 283 μg/cm2/H. Further, EthoGel formulation of ibuprofen may be associated with the following composition:

| Component | w/w % | weight (g) |
| --- | --- | --- |
| Ibuprofen | 4.0 | 40.0 |
| Ethanol | 40.0 | 400.0 |
| Glycerin | 10.5 | 105.0 |
| Polyethylene glycol | 3.0 | 30.0 |
| Xanthan gum | 1.0 | 10.0 |
| Carbomer | 0.2 | 2.0 |
| Sodium carbonate | 0.35 | 3.5 |
| Water | 41.0 | 409.5 |

Example 2 of EthoGel Formulation

When preparing this EthoGel formulation of diclofenac on a 1 kg scale, 388 g of ethanol, 200 g of glycerin, and 300 g of water may be mixed in a suitable container under stirring. Further, 7.0 g of sodium carbonate, 10.0 g of diclofenac, 8.0 g of xanthan gum, and 7.8 g of Carbomer may be added to dissolve/disperse while the mixture is under stirring. Further, a homogenizer may be used to help disperse xanthan gum and/or Carbomer if needed. After completing the addition of all the solid ingredients, stirring may be performed for 30 min, followed by slowly adding the remaining amount of water (79.2 g) under slow stirring until the mixture becomes a homogeneous gel. An in vitro permeation study for this formulation using the pig abdominal skin (thickness=0.20 cm) shows that diclofenac has a flux of 54 μg/cm2/H. Further, EthoGel formulation of diclofenac may be associated with the following composition:

| Component | w/w % | weight (g) |
| --- | --- | --- |
| Diclofenac | 1.0 | 10.0 |
| Ethanol | 38.8 | 388.0 |
| Glycerin | 20.0 | 200.0 |
| Xanthan gum | 0.80 | 8.0 |
| Carbomer | 0.78 | 7.8 |
| Sodium Carbonate | 0.70 | 7.0 |
| Water | 37.92 | 379.2 |

Figure 6:
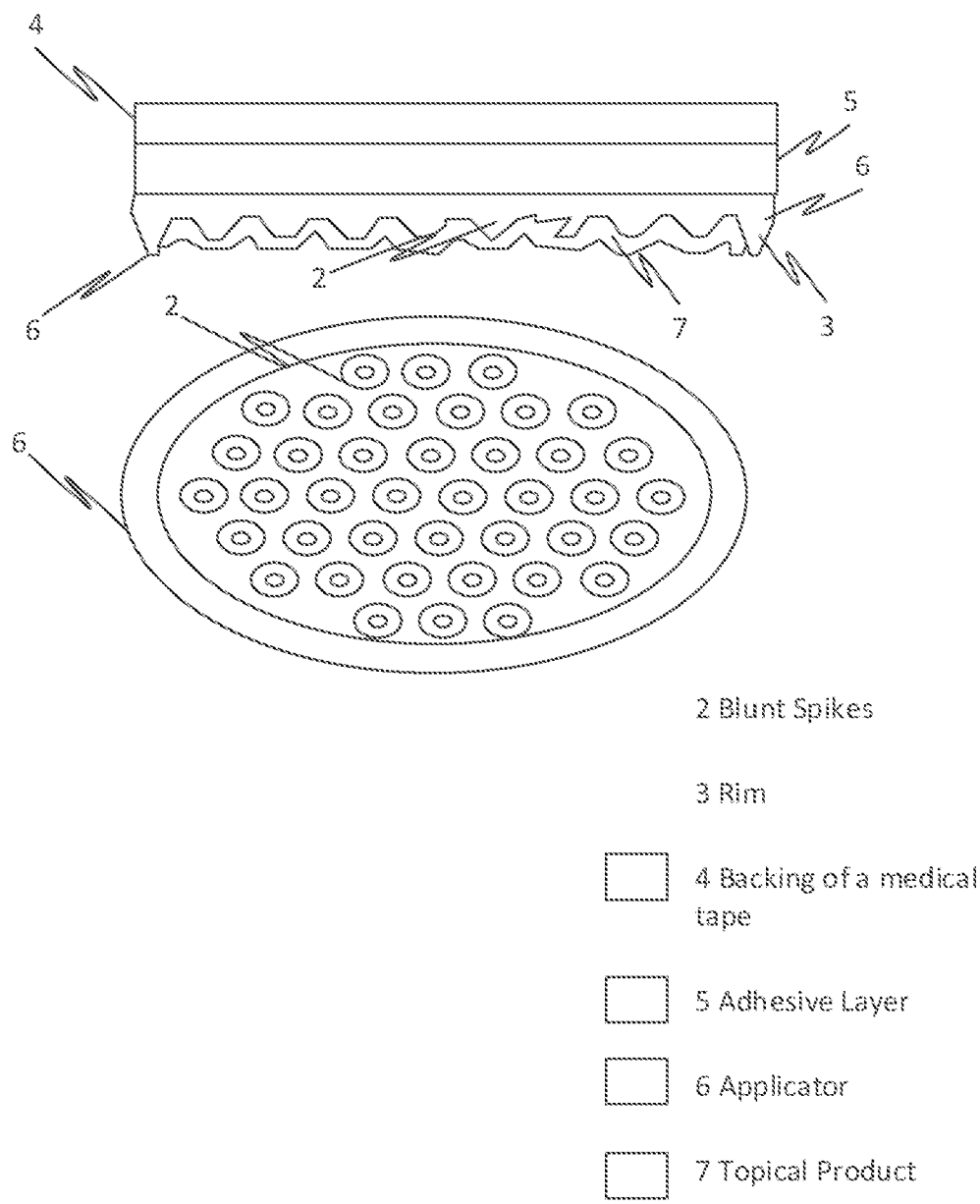
FIG. 6 is a schematic of a transdermal drug delivery system showing the structure of an applicator, in accordance with some embodiments.

Now referring to figures, FIG. 6 is a schematic of a transdermal drug delivery system showing the structure of an applicator, in accordance with some embodiments. Accordingly, the applicator 6 may include an oval-shaped disk applicator mounted on a backing layer of the medical tape 4 via an adhesive layer 5 in combination with a topical formulation. The applicator 6 and backing layer prevent the passage of drug and other components, particularly the volatile permeation enhancer(s) through the surface of the delivery system and provide support. Further, the suitable materials for the backing layer include, for example, polyester, polyethylene terephthalate, some type of nylon, polypropylene, metalized polyester films, polyvinylidene chloride, and aluminum foil (Hoeck et al., U.S. Pat. No. 6,335,030). Further, suitable materials for the adhesive layer 5 include, for example, acrylate polymer and polyisobutylene, in which zinc oxide and magnesium oxide, and the like are used as crosslinking agents for carboxylic acid groups (Burton et al., U.S. Pat. No. 5,948,433).

Further, in some embodiments, the applicator 6 may be made of plastic and/or metallic materials approved for pharmaceutical/medical device applications. Circling edge of the applicator is a rim 3, of which the height can be varied to optimize the effectiveness of the device in containing the topical formulation 7 and in drug delivery. On the surface of the applicator within the circling rim 3, there are blunt spikes 2 that can be in various numbers, sizes and shapes. The applicator 6 may be made of materials of polymers and metal foils with a suitable thickness that will maintain the desired shape while providing certain degree of flexibility. Suitable polymers may include, for example, polyesters, polycarbonates, polyethylene, polypropylene, polyvinyl chlorides, and polyethylene terephthalate. Suitable metal foils may include, for example, aluminum and stainless steel. The height of the rim 3 may be from about 600 to 3500 micrometers. The ratio between the height of the rim 3 and the height of the blunt spikes 2 are in the range of 0.5 to 1.5 and may be optimized based on the physical characteristics of the formulation and the site of application. When applied, the topical formulation 7 may fill the space on the applicator between the spikes and within the rim 3.

Figure 7:
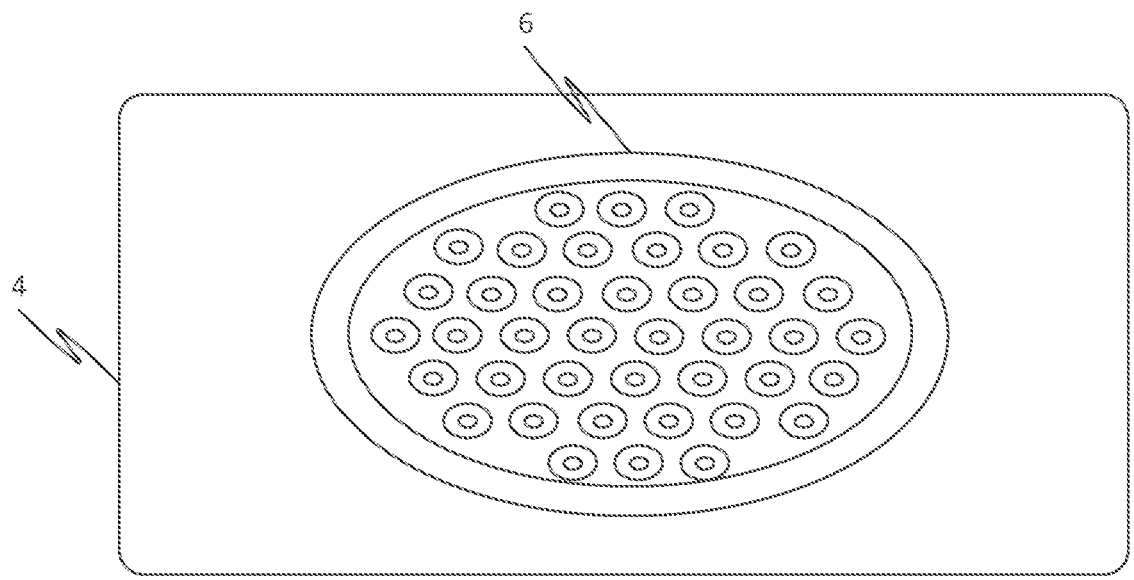
FIG. 7 is an enlarged view of a transdermal drug delivery system showing placement of the applicator on a piece of the medical tape, in accordance with some embodiments.

FIG. 7 is an enlarged view of a transdermal drug delivery system showing placement of the applicator on a piece of the medical tape, in accordance with some embodiments. Accordingly, a piece of the medical tape 4 may be used to affix the applicator 6 on the skin of a user/patient.

Figure 8:
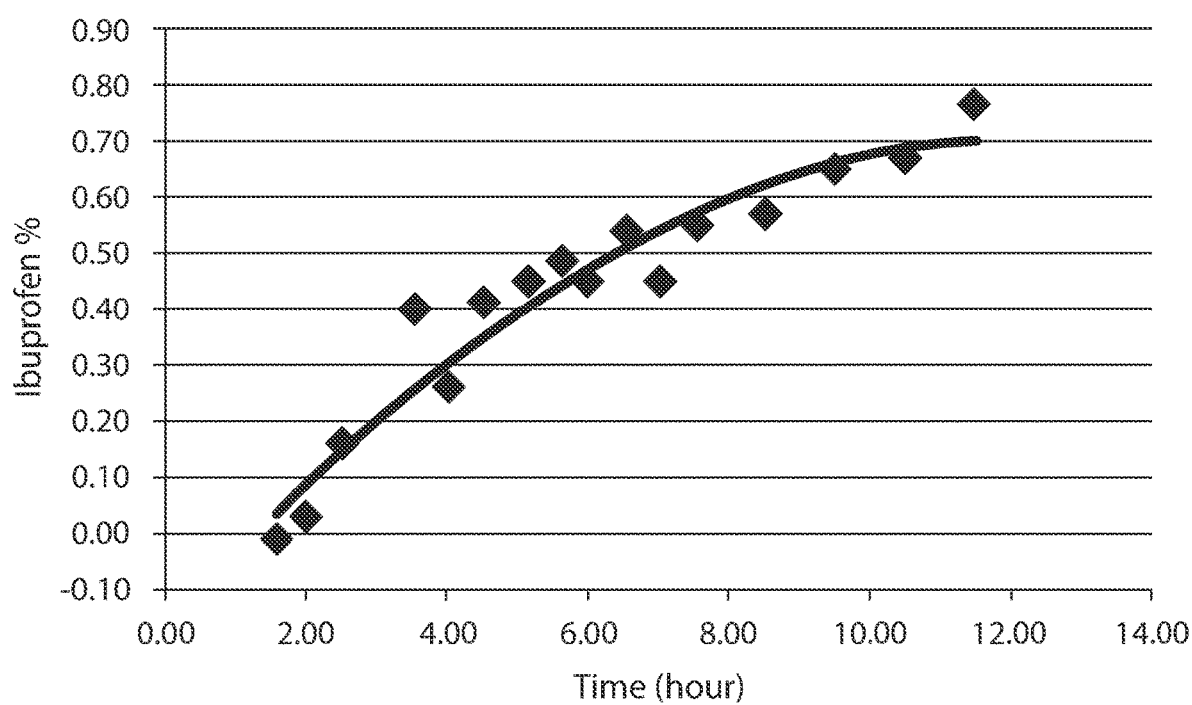
FIG. 8 is a graphical representation illustrating in vitro skin permeation of ibuprofen using Example 1 of the EthoGel formulation and pig abdominal skin, in accordance with some embodiments.

FIG. 8 is a graphical representation illustrating in vitro skin permeation of ibuprofen using Example 1 of the Etho-Gel formulation and pig abdominal skin, in accordance with some embodiments.

Figure 9:
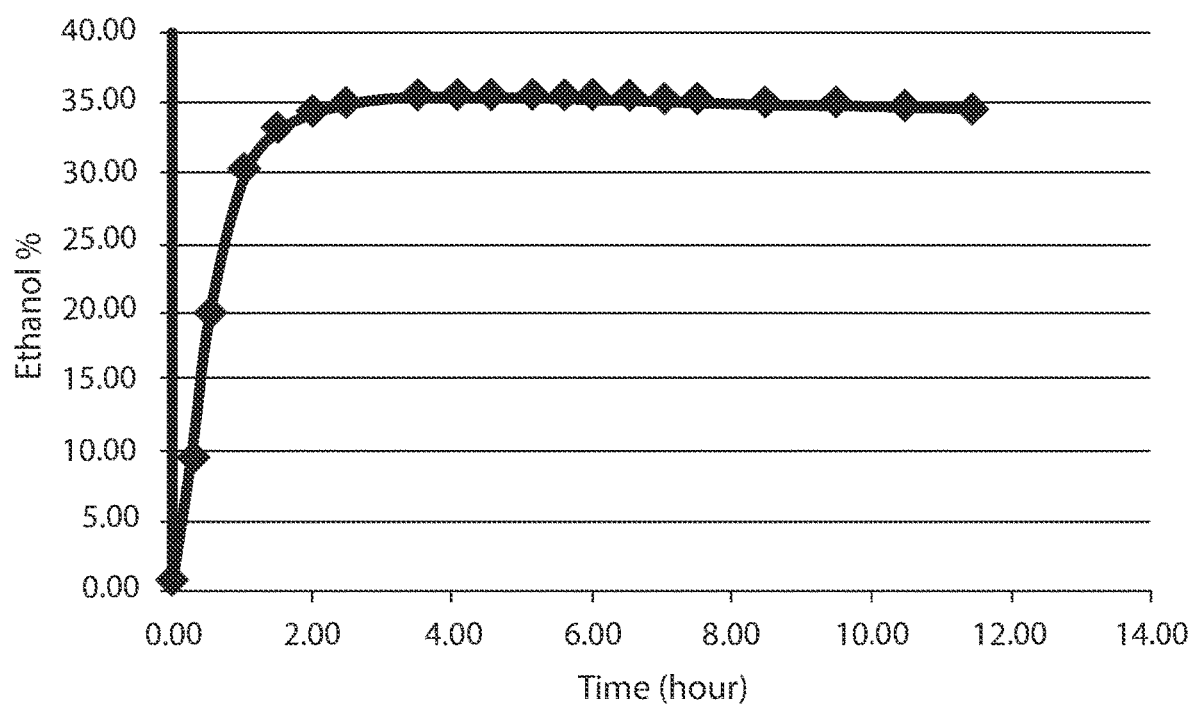
FIG. 9 is a graphical representation illustrating in vitro skin permeation of ethanol using Example 1 of EthoGel formulation and pig abdominal skin, in accordance with some embodiments.

FIG. 9 is a graphical representation illustrating in vitro skin permeation of ethanol using Example 1 of EthoGel formulation and pig abdominal skin, in accordance with some embodiments.

Figure 10:
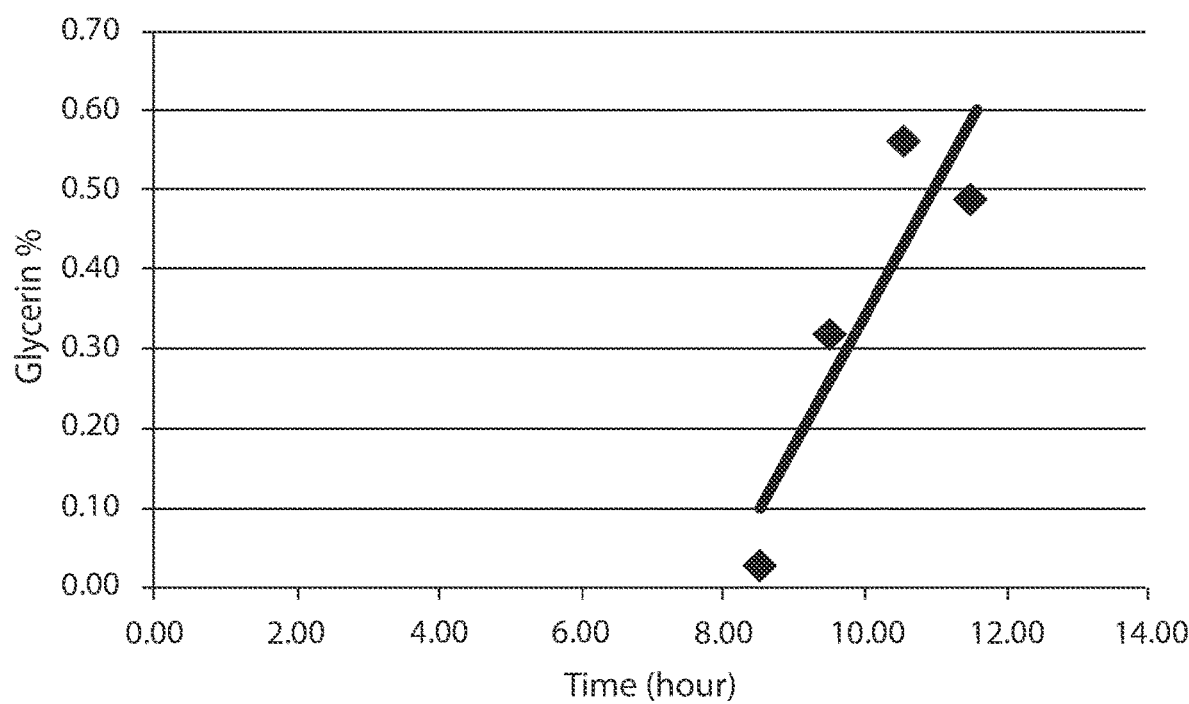
FIG. 10 is a graphical representation illustrating in vitro skin permeation of glycerin using Example 1 of EthoGel formulation and pig abdominal skin, in accordance with some embodiments.

FIG. 10 is a graphical representation illustrating in vitro skin permeation of glycerin using Example 1 of EthoGel formulation and pig abdominal skin, in accordance with some embodiments.

Figure 11:
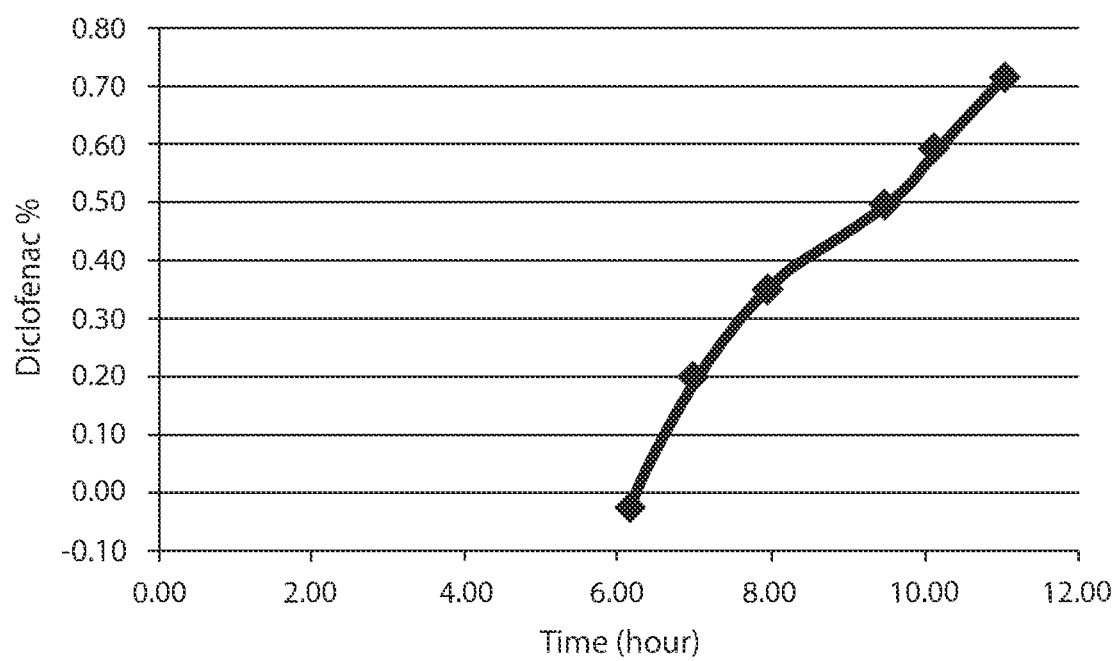
FIG. 11 is a graphical representation illustrating in vitro skin permeation of diclofenac using Example 2 of EthoGel formulation and pig abdominal skin, in accordance with some embodiments.

FIG. 11 is a graphical representation illustrating in vitro skin permeation of diclofenac using Example 2 of EthoGel formulation and pig abdominal skin, in accordance with some embodiments.

In further embodiments, a transdermal drug delivery system for delivering a drug is disclosed. Further, the transdermal drug delivery system may include an applicator 6 which is mounted on a backing layer of a medical tape 4 via an adhesive layer 5, and a topical formulation 7 comprising a suitable amount of a drug, wherein the suitable amount of drug penetrates the skin after applying the system to the skin of a patient.

Further, in some embodiments, the topical formulation 7 is an EthoGel formulation comprising (1) a suitable concentration of an active ingredient in a hydrogel-like carrier for delivering a given dose of the drug trans-dermally, (2) two gelling agents that define the carrier's hydrogel-like physical properties in the presence of (3) two skin penetration enhancers which also act as solvent/co-solvent, (4) buffering agents to further increase the solubility of the active ingredient in the formulation, (5) other stabilizers, and (6) various components with an optimized ratio to maintain chemical and physical stability of the drug delivery medium.

Further, in some embodiments, the applicator 6 may include a rim 3 to define a sealed space and blunt spikes 2 present on its surface and in the space of rim 3. Further, the topical formulation 7 may be filled in the space of the applicator 6 between the spikes and the rim 3. Further, the applicator 6 has different shapes and sizes, which can be optimized for delivering the suitable amount of the drug, and wherein the blunt spikes 2 serve the purpose of holding the topical formulation 7 and increasing the total surface area in contact with the skin when the system is applied to the patient.

In further embodiments, a method for transdermal delivery of a drug is disclosed. Further, the method may include applying the transdermal drug delivery system to the skin of a patient. Further, the transdermal drug delivery system may include the applicator 6 which is mounted on a backing layer of the medical tape 4 via adhesive layer 5, and the topical formulation 7 comprising a suitable amount of drug penetrates the skin after applying the system to the skin of the patient.

Further, in some embodiments, the topical formulation 7 is an EthoGel formulation that comprises (1) a suitable concentration of the active ingredient in a hydrogel-like carrier for delivering a given dose of the drug trans-dermally, (2) two gelling agents that define the carrier's hydrogel-like physical properties, of which the chemical/physical property, as well as amount/ratio, are optimized to ensure that the carrier will withstand the presence of a high concentration of organic solvent/co-solvents while maintaining its hydrogel-like physical property, (3) two skin penetration enhancers which also act as solvent/co-solvent and which play a critical role in accelerating the transdermal drug delivery, (4) other stabilizing agents, (5) buffering agents to further increase the solubility of the active ingredient in the formulation by adjusting pH of the formulation, and (6) various components with an optimized ratio to maintain chemical and physical stability of the drug delivery medium. Further, the hydrogel-like carrier may include two gelling agents namely xanthan gum and Carbomer, and various components known in the art, for example, water as a solvent/co-solvent, a skin penetration enhancer, a second solvent/co-solvent, a preservative, a buffering agent, or a stabilizer, which are non-toxic and which do not interact with other components of the composition.

Further, the skin penetration enhancers may include ethanol and glycerin, of which the amount and ratio are adjusted to promote the local or systemic distribution of the active ingredient. Further, the skin penetration enhancers may include other skin penetration enhancers known in the art including, for example, other alcohols, azone compounds, essential oils, sulfoxides, and fatty acid esters (Hoeck et al., U.S. Pat. No. 6,335,030).

Further, in some embodiments, the applicator 6 may include the rim 3 to define a sealed space and the blunt spikes 2 present on its surface and in the space of rim 3. Further, the topical formulation 7 is filled in the space of applicator 6 between the blunt spikes 2 and the rim 3. Further, the applicator 6 has different shapes and sizes, which can be optimized for delivering the suitable amount of the drug, and wherein the blunt spikes 2 serve the purpose of holding the topical formulation 7 and increasing the total surface area in contact with the skin when the system is applied to the patient.

Further, the EthoGel-Applicator transdermal drug delivery system (EGATDDS) described herein may be configured for delivering drugs at a much higher rate compared with the conventional TD patches and/or the conventional topical products for the following reasons: 1) carrier of the EthoGel formulation is an "OrganoGel" due to the presence of high concentration of ethanol and glycerin, which are effective skin penetration enhancers, whereas that of a conventional hydrogel utilizes water as the main solvent; 2) an optimized EthoGel formulation can reversibly alter physiological property of the skin's SC layer to allow fast drug penetration; 3) the applicator 6 creates an occlusive micro-environment which maintains the ethanol concentration in the carrier over time; 4) the applicator 6 can handle a much larger or adjustable quantity of the drug delivery system (i.e., the EthoGel formulation); 5) the choice of the media is not limited to types of adhesive systems because they are no longer an integral part of the delivery system; 6) the specially designed applicator 6 provides additional opportunities in increasing the skin contacting area as well as reducing the penetration distance for the active ingredients.

Further, the EthoGel formulation 7 of ibuprofen or diclofenac is prepared in the form of a gel, wherein the former will be used to reduce fever in infants and toddlers and the latter to manage acute/chronic pain for arthritis patients. Other topical formulations of a different active ingredient can be prepared in the form of, for example, a cream, a foam, a lotion, an ointment which can be used by the patient with different ailment, e.g., with Alzheimer's disease.

As used herein, "a" or "an" means one or more (or at least one). For example, a topical formulation 7 comprises a stabilizer and a buffering agent, which means the topical formulation 7 can contain more than one stabilizer and more than one buffering agent. "About" is used herein to refer to in the range of 20% of the target point, for example, "from about 600 to about 3500 micrometers" means from the range of 480 to 720 micrometers to the range of 2800 to 4200 micrometers.

While certain embodiments of the disclosure have been described, other embodiments may exist. Further, the disclosed methods' stages may be modified in any manner, including by reordering stages and/or inserting or deleting stages, without departing from the disclosure.

Although the invention has been explained in relation to its preferred embodiment, it is to be understood that many other possible modifications and variations can be made without departing from the spirit and scope of the invention as hereinafter claimed.

What is claimed is:

1. A transdermal drug delivery system for delivering a drug to a patient comprising:
   a backing layer;
   an adhesive layer;
   a topical applicator;
   a suitable quantity of drug;
   a quantity of topical carrier;
   a hydrogel homogenizer;
   the backing layer being a piece of medical tape;
   the topical applicator comprising a flat applicator body, a plurality of blunted spikes, and a containment rim;
   the suitable quantity of drug and the quantity of topical carrier being homogenously mixed together as a topical medication;
   the adhesive layer being positioned in between the backing layer and the flat applicator body;
   the flat applicator body being connected across and against the backing layer by the adhesive layer;
   the containment rim and the plurality of blunted spikes being positioned adjacent to the flat applicator body, opposite to the backing layer;
   the plurality of blunted spikes being connected onto the flat applicator body;
   the plurality of blunted spikes being distributed across the flat applicator body;
   the plurality of blunted spikes being oriented away from the flat applicator body;
   the containment rim being peripherally connected to the flat applicator body;
   the containment rim being positioned around the plurality of blunted spikes;
   the topical medication being retained within the containment rim;
   the topical medication being retained amongst the plurality of blunted spikes;
   the quantity of topical carrier comprising at least one quantity of gelling agent, at least one quantity of skin-penetrating enhancer, at least one quantity of buffering agent, at least one quantity of stabilizer, and a quantity of water, wherein the quantity of water is approximately 41.0 percentage by weight (wt. %) of the topical medication;
   the at least one quantity of gelling agent, the at least one quantity of skin-penetrating enhancer, the at least one quantity of buffering agent, the at least one quantity of stabilizer, and the quantity of water being homogenously mixed together with the hydrogel homogenizer;
   the suitable quantity of drug being a quantity of ibuprofen, wherein the quantity of ibuprofen is approximately 4.0 wt. % of the topical medication;
   the at least one gelling agent being a quantity of xanthan gum and a quantity of carbomer, wherein the quantity of xanthan gum is approximately 1.0 wt. % of the topical medication, and wherein the quantity of carbomer is approximately 0.2 wt. % of the topical medication;
   the at least one quantity of skin-penetrating enhancer being a quantity of ethanol and a quantity of glycerin, wherein the quantity of ethanol is approximately 40.0 wt. % of the topical medication, and wherein the quantity of glycerin is approximately 10.5 wt. % of the topical medication;
   the at least one quantity of buffering agent being a quantity of sodium carbonate, wherein the quantity of sodium carbonate is approximately 0.35 wt. % of the topical medication; and
   the at least one quantity of stabilizer being a quantity of polyethylene glycol, wherein the quantity of polyethylene glycol is approximately 3 wt. % of the topical medication.

2. The transdermal drug delivery system for delivering a drug to a patient as claimed in claim 1, wherein the backing layer is made of an impermeable material.

3. The transdermal drug delivery system for delivering a drug to a patient as claimed in claim 1, wherein the topical applicator is made of a polycarbonate material.

4. The transdermal drug delivery system for delivering a drug to a patient as claimed in claim 1, wherein the flat applicator body is sized and/or shaped to optimally deliver the suitable quantity of drug through a patient's skin.

5. The transdermal drug delivery system for delivering a drug to a patient as claimed in claim 1, wherein a perimeter shape of the flat applicator body is selected from a group consisting of: a square shape, a rectangular shape, a circular shape, and an oblong shape.

6. The transdermal drug delivery system for delivering a drug to a patient as claimed in claim 1, wherein a height of the containment rim from the flat applicator body is between 600 micrometers ($\mu$m) to 3500 $\mu$m.

7. The transdermal drug delivery system for delivering a drug to a patient as claimed in claim 1, wherein a total number of blunted spikes for the plurality of blunted spikes is configured to optimally deliver the suitable quantity of drug through a patient's skin.

8. A transdermal drug delivery system for delivering a drug to a patient comprising:
   a backing layer;
   an adhesive layer;
   a topical applicator;
   a suitable quantity of drug;
   a quantity of topical carrier;
   a hydrogel homogenizer;
   the backing layer being a piece of medical tape;
   the topical applicator comprising a flat applicator body, a plurality of blunted spikes, and a containment rim;
   the suitable quantity of drug and the quantity of topical carrier being homogenously mixed together as a topical medication;
   the adhesive layer being positioned in between the backing layer and the flat applicator body;
   the flat applicator body being connected across and against the backing layer by the adhesive layer;
   the containment rim and the plurality of blunted spikes being positioned adjacent to the flat applicator body, opposite to the backing layer;
   the plurality of blunted spikes being connected onto the flat applicator body;
   the plurality of blunted spikes being distributed across the flat applicator body;

the plurality of blunted spikes being oriented away from the flat applicator body;

the containment rim being peripherally connected to the flat applicator body;

the containment rim being positioned around the plurality of blunted spikes;

the topical medication being retained within the containment rim;

the topical medication being retained amongst the plurality of blunted spikes;

the quantity of topical carrier comprising at least one quantity of gelling agent, at least one quantity of skin-penetrating enhancer, at least one quantity of buffering agent, and a quantity of water, wherein the quantity of water is approximately 37.92 percentage by weight (wt. %) of the topical medication;

the at least one quantity of gelling agent, the at least one quantity of skin-penetrating enhancer, the at least one quantity of buffering agent, and the quantity of water being homogenously mixed together with the hydrogel homogenizer;

the suitable quantity of drug being a quantity of diclofenac, wherein the quantity of diclofenac is approximately 1.0 wt. % of the topical medication;

the at least one gelling agent being a quantity of xanthan gum and a quantity of carbomer, wherein the quantity of xanthan gum is approximately 0.80 wt. % of the topical medication, and wherein the quantity of carbomer is approximately 0.78 wt. % of the topical medication;

the at least one quantity of skin-penetrating enhancer being a quantity of ethanol and a quantity of glycerin, wherein the quantity of ethanol is approximately 38.8 wt. % of the topical medication, and wherein the quantity of glycerin is approximately 20.0 wt. % of the topical medication; and the at least one quantity of buffering agent being a quantity of sodium carbonate, wherein the quantity of sodium carbonate is approximately 0.70 wt. % of the topical medication.

9. The transdermal drug delivery system for delivering a drug to a patient as claimed in claim 8, wherein the backing layer is made of an impermeable material.

10. The transdermal drug delivery system for delivering a drug to a patient as claimed in claim 8, wherein the topical applicator is made of a polycarbonate material.

11. The transdermal drug delivery system for delivering a drug to a patient as claimed in claim 8, wherein the flat applicator body is sized and/or shaped to optimally deliver the suitable quantity of drug through a patient's skin.

12. The transdermal drug delivery system for delivering a drug to a patient as claimed in claim 8, wherein a perimeter shape of the flat applicator body is selected from a group consisting of: a square shape, a rectangular shape, a circular shape, and an oblong shape.

13. The transdermal drug delivery system for delivering a drug to a patient as claimed in claim 8, wherein a height of the containment rim from the flat applicator body is between 600 micrometers (μm) to 3500 μm.

14. The transdermal drug delivery system for delivering a drug to a patient as claimed in claim 8, wherein a total number of blunted spikes for the plurality of blunted spikes is configured to optimally deliver the suitable quantity of drug through a patient's skin.

* * * * *